United States Patent [19]

Hanley et al.

[11] Patent Number: 5,741,898
[45] Date of Patent: Apr. 21, 1998

[54] DNA SEQUENCE ENCODING NICOTIANA SQUALENE SYNTHETASE

[76] Inventors: Kathleen Marie Hanley, 309 Saddlebrook Cir., Lewisville, N.C. 27023; Gary Mark Hellmann, 3516 Donegal Dr., Clemmons, N.C. 27012; Olivier Nicolas, 2700 Reynolda Rd., Apartment 1215, Winston-Salem, N.C. 27106

[21] Appl. No.: 310,693

[22] Filed: Sep. 22, 1994

[51] Int. Cl.$^6$ .......................... C12N 15/54; C12N 15/29; C12N 9/10; C12N 15/70

[52] U.S. Cl. ............... 536/23.2; 435/193; 435/320.1; 536/23.6

[58] Field of Search .................... 435/69.1, 193, 435/252.3; 536/23.2, 23.6

[56] References Cited

U.S. PATENT DOCUMENTS

| | | | |
|---|---|---|---|
| 4,652,639 | 3/1987 | Stabinsky | 435/91.52 |
| 4,757,006 | 7/1988 | Toole, Jr. et al. | 435/69.6 |
| 5,223,419 | 6/1993 | Katagiri et al. | 435/172.3 |
| 5,290,926 | 3/1994 | Scheidegger et al. | 536/23.2 |
| 5,349,126 | 9/1994 | Chappell et al. | 800/205 |
| 5,362,864 | 11/1994 | Chua | 536/23.6 |
| 5,389,609 | 2/1995 | Woloshuk et al. | 514/12 |

FOREIGN PATENT DOCUMENTS

| | | | |
|---|---|---|---|
| 486 290 | 5/1992 | European Pat. Off. | C12N 15/81 |
| 2249099 | 4/1992 | United Kingdom . | |
| 2 272 442 | 5/1994 | United Kingdom | C12N 9/10 |
| 9317757 | 9/1993 | WIPO . | |

OTHER PUBLICATIONS

Kuswik–Rabiega et al., Squalene Synthetase, "Solubilization and Partial Purification of Squalene Synthetase, Copurification of Presqualene Pyrophosphate and Squalene Synthetase Activities," *Journal of Biological Chemistry*, vol. 262, pp. 1505–1509 (1987).

Summers et al., "Cloning, expression and characterization of the cDNA encoding human hepatic squalene synthase, and its relationship to phytoene synthase," *Gene*, vol. 136, pp. 185–192 (1993).

Keller et al., Research Report, "Identification and Regulation of Rat Squalene Synthetase mRNA[1]," *Archives of Biochemistry and Biophysics*, vol. 302, No. 1, Apr., pp. 304–306 (1993).

LoGrasso et al., "Overexpression, Purification, and Kinetic Characterization of a Carboxyl–Terminal–Truncated Yeast Squalene Synthetase," *Archives of Biochemistry and Biophysics*, vol. 307, No. 1, Nov. 15, pp. 193–199 (1993).

McKenzie et al., "Molecular Cloning, Expression, and Characterization of the cDNA for the Rat Hepatic Squalene Synthase," *The Journal of Biological Chemistry*, vol. 267, pp. 21368–21374 (1992).

Robinson et al., "Conservation between Human and Fungal Squalene Synthetases: Similarities in Structure, Function, and Regulation," *Molecular and Cellular Biology*, vol. 13, No. 5, May 1993, pp. 2706–2717.

Jennings et al., "Molecular cloning and characterization of the yeast gene for squalene synthetase," *Proc. Natl. Acad. Sci. USA*, Cell Biology, vol. 88, pp. 6038–6042, Jul. 1991.

Jaye, M., et al., 1983, Nucleic Acids Research 11(8):2325–2335.

Ullrich, A., et al., 1984, The EMBO Journal, 3(2):361–364.

Lathe, R., 1985, Journal of Molecular Biology 183(1):1–12.

Wada, K., et al., Nucleic Acids Research, 19(Supplement): 1981–1986.

(List continued on next page.)

*Primary Examiner*—Keith D. Hendricks
*Assistant Examiner*—William W. Moore

[57] ABSTRACT

A DNA sequence isolated form a Nicotiana species (e.g., *Nicotiana benthamiana*) has SEQ ID NO: 1. The DNA sequence encodes a polypeptide having enzymatic activity for producing squalene. The polypeptide is referred to as squalene synthetase.

11 Claims, 4 Drawing Sheets

OTHER PUBLICATIONS

Fortkamp, E., et al., DNA, 5(6): 511–517.

Frohman, M.A., et al., Proceedings of the National Academy of Sciences, U.S.A., 85(23):8998–9002.

Hanley, K., et al., 1992, Plant Physiology, 98(1):215–220.

Zhang, D., et al., 1993, Archives of Biochemistry and Biophysics, 304(1):133–143.

Vögeli, U., et al, 1988 Plant Physiology, 88: 1291–1296.

Threlfall, D.R., et al., 1988, Phytochemistry, 27(8):2567–2580.

Hanley, K.M., et al., 1992, in *Secondary Metabolitic Biosynthesis and Metabolism*, McCormick, S.P. and, Petroski, R.J. Eds., Plenum Press, New York, pp. 329–336.

Chappell, J., et al., 1989, Plant Cell Reports, 8(1):48–52.

Jiang, G. et al., 1993, The Journal of Biological Chemistry, 268(17): 12818–12824.

P.J. Facchini and J. Chappell; *Gene family for an elicitor-induced sesquiterpene cyclase in tobacco;* Proc. Natl. Acad. Sci. 89 pp. 11088–11092 (1992).

DNA SEQUENCE ENCODING NICOTIANA SQUALENE SYNTHETASE

BACKGROUND OF THE INVENTION

The present invention relates to genetic engineering, particularly relating to nucleic acid sequences encoding enzymes useful in isoprenoid biosynthesis; and specifically to DNA sequences encoding enzymes involved in catalyzing the biosynthesis of squalene.

Squalene is a 30-carbon triterpene composed of six isoprene units. Squalene is an intermediate in the biosynthesis of sterols, such as, cholesterol. See, Bradfute et al., *J. Biol. Chem.*, Vol. 267, p. 18308 (1992) and Ericsson et al., *J. Biol. Chem.*, Vol. 267, p. 18708 (1992). Squalene synthetase, an enzyme that resides at a branch in sterol biosynthesis, catalyzes the formation of squalene via reductive dimerization of the 15-carbon intermediate farnesyl diphosphate (FPP). This reaction is the first committed step in sterol biosynthesis. Alternatively, FPP may serve as substrate for numerous other prenyltransferases leading to the prenylation of proteins, or to the formation of non-sterol isoprenoids such as dolichols, ubiquinones, and carotenoids. See, Kuswik-Rabiega et al., *J. Biol. Chem.*, Vol. 262, p. 1505 (1987), Summers et al., *Gene*, Vol. 136, p. 185 (1993); Keller et al., *Arch. Biochem. Biophys.*, Vol. 302, p. 304 (1993); LoGrasso et al., *Arch. Biochem. Biophys.*, Vol. 307, p. 193 (1993); McKenzie et al., *J. Bio. Chem.*, Vol. 267, p. 21368 (1992); European Patent Application No. 486,290 and G.B. Patent Application Nos. 2,249,099 and 2,272,442.

Squalene synthetase has been studied in mammalian systems, and is considered a key enzyme in the regulation of cholesterol biosynthesis. Thus, squalene synthetase has been studied as a possible target for the design of therapeutics aimed at controlling serum cholesterol levels. See, Robinson et al., *Mol. Cell. Biol.*, Vol. 13, p. 2706 (1993). Inhibitors of the enzyme 3-hydroxy-3-methylglutaryl-CoA reductase (HMG-CoA reductase) have been shown to reduce serum cholesterol levels. See, Goldstein et al., *Nature*, Vol. 343, p 425 (1990) and Brown, et al., *J. Biol. Chem.*, Vol. 253, p. 1121 (1978). However, because HMG-CoA reductase mediates an early step in the isoprenoid pathway, the potential exists for the depletion of other key isoprenoids derived from mevalonic acid. Selective inhibition of squalene synthetase on the other hand, should not directly suppress biosynthesis of these non-sterol isoprene metabolites. Consequently, inhibitors of squalene synthetase may have advantages over inhibitors which act further upstream in the pathway. A thorough knowledge of the structure and activity of this enzyme would greatly facilitate the design of specific modulators of squalene synthetase.

Squalene has been found to have useful applications as coatings, as set forth in U.S. Pat. Nos. 5,198,254 to Nisperos-Carriedo et al. and 5,284,508 to Shibata et al., in the cosmetics industry, as is set forth in U.S. Pat. Nos. 4,699,930 to Suga and 5,116,607 to Jones; and in the pharmaceutical industry, as is set forth in U.S. Pat. No. 4,806,352 to Cantrell and 5,260,067 to Zheng Xu. Squalene synthetase inhibitors are set forth in Dufresne et al., *Tetrahedron*, Vol. 48, p. 10221 (1992); Hensens et al., *Tetrahedron Let.*, Vol. 34, p. 399 (1993) and U.S. Pat. Nos. 5,250,424 to Bills et al., 5,2252,471 to Byrne et al. and 5,278,067 to Dawson et al..

It would be highly desirable to have the capability to alter those biosynthetic pathways which involve squalene, particularly in higher plants such as Solanaceae. As such, it would be desirable to provide nucleotide sequences that encode enzymes (e.g., squalene synthetase), which are useful in the biosynthetic pathway of squalene, and various other isoprenoids including sterols. In particular, it would be desirable to provide the nucleotide sequences that encode squalene synthetase from a higher plant species, such as a Nicotiana species.

SUMMARY OF THE INVENTION

The present invention relates to nucleotide sequences (i.e., DNA and RNA) capable of encoding a polypeptide which has enzymatic activity for producing squalene. Such a polypeptide is referred to as squalene synthetase. The DNA is isolated from a plant (e.g., a higher plant), in particular from a Nicotiana species (e.g., *Nicotiana benthamiana*). The nucleotide sequence encodes squalene synthetase, and variants of that sequence encodes enzymes exhibiting the same biological activity as squalene synthetase. The nucleotide sequence corresponds to, or substantially to, that sequence specified by SEQ ID NO: 1. The nucleotide sequence may be provided in an isolated, substantially pure form.

In another aspect, the present invention relates to a polypeptide which may be provided in a purified (e.g., isolated and substantially pure) form. The polypeptide has enzymatic activity for producing squalene. That polypeptide is encoded by the nucleotide sequence which corresponds to, or substantially to, that sequence specified by SEQ ID NO: 1. The polypeptide has an amino acid sequence which 6corresponds to, or substantially to, the amino acid sequence specified by SEQ ID NO: 2. Polypeptides having amino acid sequences which correspond substantially to that encoded by the specified nucleic acid sequence have different amino acid sequences (e.g., a minor number of amino acids of the sequence can be deleted, added or substituted), but the same type of biological activities as that encoded by the specified sequence, although those biological activities may differ in degree.

In another aspect, the present invention relates to fragments of polypeptides (e.g., polypeptide derivatives) encoded by nucleotide sequences which correspond to, or substantially to, certain nucleotide subsequences contained within that sequence specified by SEQ. ID NO: 1. Such fragments represent domains of the full length (i.e., intact) polypeptides. Such fragments can be, for example, transit peptides useful for directing polypeptides to subcellular compartments, or polypeptide domains having properties such as catalytic activity, substrate binding activity, or the like.

The nucleotide sequence of the present invention can be incorporated (i.e., in an operative fashion) into heterologous systems (e.g., yeast, bacteria or certain plants) in order that the respective polypeptide can be synthesized thereby. The nucleotide sequence can be incorporated into plants (e.g., rice, corn, tobacco or tomato) using transformation techniques or viral gene expression systems. The RNA molecules or polypeptides encoded by those nucleotide sequences can be used to alter the biosynthetic pathway of (i) sterols (e.g., cycloartenol, cholesterol, obtusifoliol, and related compounds), or (ii) other isoprenoids (e.g., squalene, phytoene, lycopene, beta-carotene, and related compounds). For example, the nucleotide sequence can be incorporated into a heterologous system in order to effect the accumulation in that system of various isoprenoids, including squalene. Alternatively, the polypeptides can be isolated in order to be used as enzymes in the in vitro synthesis of sterols or isoprenoids.

In another aspect, the present invention relates to recombinant DNA or RNA molecules. Such molecules include DNA sequences, corresponding RNA sequences, or subsequences of such DNA and RNA sequences. Certain sequences and subsequences (e.g., promoters, enhancers, terminators and replication signals) are capable of facilitating the expression of squalene synthetase. A DNA sequence or at least one subsequence has a nucleotide sequence which is specified, or substantially specified, by at least a portion of that nucleotide sequence specified by SEQ ID NO: 1. The DNA sequence is isolated from a Nicotiana species, such as *Nicotiana benthamiana*.

The recombinant molecule can be considered a plasmid or a vector. The recombinant molecule can be a plasmid or vector tailored for transfer of the recombinant molecule to plant or other cells. Recombinant molecules also can be contained in a transgenic plant cell, such as a tobacco plant cell.

In another aspect, the invention relates to the delivery and expression of sequences or subsequences as described by SEQ ID No: 1 via transient virus-based gene delivery systems. Such a system is described in European Patent Application No. 406,267 and U.S. Pat. No. 5,316,931, which are incorporated herein by reference. Such a system involves delivery of a selected nucleotide sequence as part of, or in conjunction with, a self-replicating DNA or RNA molecule (i.e., a virus), such that the exogenous gene is replicated and expressed during the course of replication and expression of viral or virus-based nucleic acids and proteins. Such gene delivery systems may be used for expression of nucleic acid sequences or subsequences as described by SEQ ID NO: 1 in either sense orientation for the expression of polypeptides, or in antisense orientation for the delivery of RNA molecules capable of inhibiting expression of the target gene or other homologous genes. Genes or gene sequences delivered in such a manner are considered to be functionally inserted in the target organism such as a tobacco plant.

A further aspect of the present invention is a crop composed of a plurality of plants having the nucleotide sequence of the present invention, or a subsequence thereof, functionally inserted therein; and planted together in an agricultural field, including a greenhouse or growth chamber.

Compositions including genetic sequences and subsequences encoding enzymes for expression in plants, such as tobacco plants, impart those plants with the ability to produce altered levels of sterols and/or isoprenoids. As such, there is provided a method for altering the synthesis of sterols and isoprenoids in plants, which method involves inserting a recombinant genetic construct into plant cells. Such a construct can provide for synthesis of naturally occurring sterols (e.g., cycloartenol, obtusifoliol or cholesterol) and other isoprenoids (e.g., squalene, phytoene or beta-carotene) within such plant cells. For example, certain recombinant genetic constructs of the present invention are capable of increasing or decreasing expression of at least one naturally occurring enzyme in order that resulting transformed plants exhibit enhanced ability to produce a sterol or a carotenoid. As such, there is provided a method for altering the biosynthetic pathway of various components in plants.

In yet another aspect, the present invention relates to an antisense sequence for that sequence which corresponds to, or substantially to, the totality or a subset of that nucleic acid sequence specified by SEQ ID NO: 1. As such, that sequence encodes RNA molecules capable of inhibiting expression of the corresponding gene and genes related thereto. Antisense RNA is capable of reducing the expression of genes within plant cells. See, Ecker et al., *Proc. Nat. Acad. Sci. USA*, Vol. 83, p. 5372, (1986) and Rothstein et al., *Proc. Nat. Acad. Sci. USA*, Vol. 84, p. 8439 (1987). The nucleotide sequence can be incorporated into plants (e.g., tobacco or tomato) using transformation techniques or viral gene expression systems. As a result, the present invention provides for a method for altering the synthetic pathway of sterols and isoprenoids. For example, the expression of an antisense molecule can be useful for suppressing or preventing synthesis of sterols (e.g., to cause a flux of total carbon available for biosynthesis of carotenoid compounds) or for preventing synthesis of certain isoprenoid compounds. Alternatively, expression of an antisense molecule may be useful in accumulating relatively high levels of certain molecules upstream of a particular metabolic block. Another example is the use of such antisense molecules to deliberately direct metabolites toward one branch of a branched pathway, such as that pathway involved in carotenoid biosynthesis.

DETAILED DESCRIPTION OF THE PREFERRED EMBODIMENTS

The nucleotide sequences of genetic materials of the present invention are isolated from a plant, and preferably from a Nicotiana species. A plant is an organism belonging to the kingdom Plantae. See, Raven, et al., p. 178 (1981). Most preferably, the nucleotide sequences are isolated from *Nicotiana benthamiana*. Examples of other Nicotiana species include *Nicotiana debnevi*, *Nicotiana glauca*, *Nicotiana glutinosa*, *Nicotiana rustica*, *Nicotiana svaveolens* and *Nicotiana tabacum*. Examples of cultivars of *Nicotiana tabacura* include flue-cured tobacco (e.g., NK 326), Burley tobacco (e.g., KY 14) and Maryland tobacco (e.g., MD 609).

The nucleotide sequence of isolated genetic material of the present invention can be obtained by a variety of techniques. The sequence can be obtained by sequencing non-vector nucleotide sequences of recombinant molecules. Nucleotide sequence information can be obtained by employing widely used DNA sequencing protocols. Examples of suitable nucleotide sequencing protocols can be found in Berger and Kimmel, *Methods in Enzymology Vol. 51, Guide to Molecular Cloning Techniques*, Academic Press (1987). Nucleotide sequence information from several recombinant DNA isolates, including isolates from both cDNA and genomic libraries, can be combined so as to provide the entire amino acid coding sequence, as well as the nucleotide sequences of upstream and downstream nucleotide sequences.

For gene isolation, mRNA is converted into cDNA, and the resulting cDNA is cloned. The cloned cDNA then can be used directly, or it, or sequences derived from it, can be utilized for acquiring the entire gene, either (i) from a library (e.g., in a lambda or plasmid vector) using sequence information to screen the library and detect the desired clone, or (ii) by amplification with PCR (polymerase chain reaction) and subsequent cloning into a suitable vector. For example, the 5 ' and 3' RACE (Rapid Amplification of cDNA Ends) reactions can be used to clone overlapping 5' and 3' ends of the gene of interest with subsequent assembly of the complete gene.

Nucleotide sequences obtained from sequencing specific genetic library isolates can be subjected to further analysis in order to identify regions of interest in the genetic material. These regions of interest include additional open reading frames, promoter sequences, termination sequences, and the like.

Isolated DNA can be characterized as being selected from the group consisting of:

(a) Isolated DNA consisting of DNA having the nucleotide sequence which corresponds to, or substantially to, SEQ ID NO: 1.

(b) Isolated DNA which hybridizes to isolated DNA of (a) above which encodes an enzyme or fragment thereof having squalene biosynthetic activity. Hybridization of such sequences may, for example, be carried out under stringent conditions (e.g., conditions represented by a wash stringency of 0.1×SSC (1×SSC is 0.3M NaCl, 0.03M sodium citrate), 0.1% SDS at 60° C to DNA of (a) above) in a standard in situ hybridization assay. See J. Sambrook et al., *Molecular Cloning: A Laboratory Manual 2d Ed.*), Cold Spring Harbor Laboratory, Cold Spring Harbor, N.Y. (1989). In general, such sequences will be at least 95% homologous, often at least 98% homologous, and even at least 99% homologous with the sequences of (a) above.

(c) Isolated DNA homologous to isolated DNA of (a) and (b) above. Homology relates to substantial or complete identity of nucleic acid sequences. Two nucleic acid fragments are homologous if they are capable of hybridizing to one another under hybridization conditions described in Maniatis et al., *Molecular Cloning: A Laboratory Manual*, Cold Spring Harbor Laboratory, Cold Spring Harbor, N.Y., pp. 324–325 (1982). Homologous sequences can be identified that contain less than about 5% base pair mismatches by using the following wash conditions: 2 × SSC, 0.1% SDS, room temperature twice, 30 minutes each; then 2 × SSC, room temperature twice, 10 minutes each. Homology can be assessed using computer programs such as DNASIS™ and PCGene (LKB, Hitachi Corporation, Japan, and Intelligenetics, Palo Alto, Calif.) whereby the degree of homology is within the limits of homology considered significant by Bost et al., *Biochem. Biophys. Res. Commun.*, Vol. 128, pp. 1373–1380 (1985). More preferably, homologous nucleic acid strands contain less than 2% base pair mismatches, even more preferably less than 1% base pair mismatches. These degrees of homology can be selected by using more stringent wash conditions for identification of clones from gene libraries (or other sources of genetic material), as is well known in the art.

(d) Isolated DNA differing from the isolated DNA of (a), (b) and (c) above in nucleotide sequence due to the degeneracy of the genetic code, and which encodes either (i) a polypeptide identical to the polypeptide specified by SEQ ID NO: 2, or (ii) an enzyme or fragment thereof having sterol or isoprenoid biosynthetic activity.

There is about 43 to about 49 percent conservation between the nucleotide coding region specified by SEQ ID NO: 1 and those squalene synthetase genes set forth in Jennings, et al., *Proc. Nat. Acad. Sci. USA*, Vol. 88, p. 6038 (1991), McKenzie, et al., *J. Biol. Chem.*, Vol. 267, p. 21368 (1992) and Robinson, et al., *Mol. Cell. Biol.*, Vol. 13, p. 2706 (1993); as determined by PC/GENE Multiple Sequence Alignment program (IntelliGenetics, Inc., Mountain View, Calif.). With regards to the polypeptide encoded by the nucleic acid sequence specified by SEQ ID NO: 1, there is a 21.8 percent identity and 24.6 percent similarity between the amino acid sequence specified by SEQ ID NO: 2 and the squalene synthetase sequences set forth in Jennings, et al., *Proc. Nat. Acad. Sci. USA*, Vol. 88, p. 6038 (1991), McKenzie, et al., *J. Biol. Chem.*, Vol. 267, p. 21368 (1992) and Robinson, et al., *Mol. Cell. Biol.*, Vol. 13, p. 2706 (1993). However, there is 90 percent homology between the conserved residues found in known squalene synthetase amino acid sequences and those regions of homology found in the amino acid sequence specified by SEQ ID NO: 2. For the sequence specified by SEQ ID NO: 2, the conserved regions of amino acids are in positons 1, 40, 44, 48–52, 54, 55, 58, 63, 66, 69–71, 73, 74, 77, 78, 80–82, 90, 94, 97, 106, 108, 116, 122, 132, 136, 140, 147, 148, 150–152, 168–177, 179, 180, 200–214, 216, 217, 225, 227–229, 231, 233, 236, 248, 255, 262–264, 266, 267, 269, 271–273, 283, 285–294, 296–298, 303, 306, 311, 312, 314, 316, 350, 351.

The nucleotide sequences of the present invention are capable of encoding polypeptides having enzymatic activity for sterol biosynthesis and isoprenoid biosynthesis. Such polypeptides have domains of amino acid sequences having catalytic activity. The catalytic domains demonstrate enzymatic activity, can be isolated, and can be expressed in in vivo or in vitro systems.

A polypeptide derivative of a particular biosynthetic enzyme can differ in length from the natural enzyme, but typically contains numerous amino acids from the natural enzyme in the same primary order as found in that enzyme as obtained from a natural source. Such a polypeptide molecule has substantially the same full length amino acid sequence as the natural enzyme but possesses minor amino acid substitutions that do not substantially affect the ability of that derivative to cause biosynthesis of sterols or isoprenoids. Derivatives include glycosylated forms, aggregative conjugates with other enzyme molecules and covalent conjugates with unrelated chemical moieties. Covalent derivatives are prepared by linkage of functionalities to groups which are found in the enzyme amino acid chain or at the N- or C-terminal residue by means known in the art.

Isolated nucleotide sequences encoding biosynthetic enzyme can be used to produce purified enzyme or derivatives thereof by either recombinant DNA methodology or by in vitro polypeptide synthesis techniques. Purified and isolated polypeptide or nucleotide sequences are present in the substantial absence of other biological macromolecules of the same type. Purified genes and polypeptides of the present invention typically have at least 95% by weight, more preferably at least 99% by weight, and most preferably at least 99.8% by weight, of biological macromolecules of the same type present; but water, buffers, and other small molecules, especially molecules having a molecular weight of less than 1000, can be present.

Biosynthetic enzymes and polypeptide derivatives of those enzymes can be expressed by recombinant techniques when a DNA sequence encoding the relevant molecule is functionally inserted into a vector (e.g., in proper reading frame and orientation, as is well understood by those skilled in the art). Typically, the relevant gene will be inserted downstream from a promoter and will be followed by a stop codon, although production as a hybrid protein followed by cleavage may be used, if desired. In general, host-cell-specific sequences improving the production yield of enzyme and enzyme derivatives can be used, and appropriate control sequences (e.g., enhancer sequences, polyadenylation sequences, and ribosome binding sites) can be added to the expression vector.

A genetic construct can be prepared and used to transform plant cells. The transformed plant cells may be cells in culture, may be present as a disorganized mass in callus, leaf explants, or shoot cultures, or may be a post-transformation differentiated plant or plant part, such as seeds, leaves, roots, or the like. The foreign construct normally is present in all or substantially all of the cells of the plant tissue, but expression may be limited to particular cells or particular times in the development of the plant. The foreign construct normally includes transcriptional and translational initiation and termination signals, with the initiation signals 5' to the gene of interest and the termination signals 3' to the gene of interest.

The transcriptional initiation region which includes an RNA polymerase binding site (i.e., promoter) may be native to the host or may be derived from an alternative source, where the region is functional in the plant host.

The transcriptional initiation regions may include, in addition to the RNA polymerase binding site, regions providing for regulation of transcription. The 3' termination region may be derived from the same gene as the transcriptional initiation region or from a different gene. For example, where the gene of interest has a transcriptional termination region functional in the host species, that region may be retained with the gene.

An exemplary expression cassette can be constructed to include a) a transcriptional initiation region, b) the biosynthetic enzyme gene under the transcriptional regulational control of the transcriptional initiation region, c) the translational initiation codon, d) the coding sequence of the gene, with or without introns, and e) the translational stop codons, followed by f) the transcriptional termination region. The transcriptional termination region includes the terminator, and may include a polyadenylation signal sequence, and other sequences associated with transcriptional termination. The direction is 5'-3' in the direction of transcription.

When the expression product of the gene is to be located in a subcellular or extracellular compartment other than the cytoplasm, the gene usually is constructed to include particular amino acid sequences which result in translocation of the product to a particular site. That site may be an organelle, such as the chloroplast, mitochondrion, endoplasmic reticulum or nucleus, the cell plasma membrane, or may be secreted into the periplasmic space or into the external environment of the cell. Various secretory leaders, membrane integrator sequences, and translocation sequences for directing the peptide expression product to a particular site are described in the literature. See, for example, Cashmore et al., *Biotechnology,* Vol. 3, pp. 803–808 (1985), and Wickher and Lodish, *Science,* Vol. 230, pp. 400–407 (1985).

The expression cassette normally is carried on a vector having at least one replication system. For convenience, it is common to have a replication system function in *E. coli* such as ColE1, pSC101, pA-CYC184, or the like. In this manner, at each stage after each manipulation, the resulting construct may be cloned, sequenced, and the correctness of the manipulation determined.

In addition to the replication system, there frequently is at least one marker present, which may be useful in one or more hosts, or different markers for individual hosts. That is, one marker may be employed for selection in a prokaryotic host, while another marker may be employed for selection in a eukaryotic host, particularly the plant species host. The markers may be protection against a biocide, such as antibiotics, toxins, heavy metals, or the like; or complementation, imparting prototropy to an auxotrophic host.

The various fragments comprising the various constructs, expression cassettes, markers, and the like may be introduced consecutively by restriction enzyme cleavage of an appropriate replication system, and insertion of the particular construct or fragment into the available sites. After ligation and cloning, the vector may be isolated for further manipulation. All of these techniques are amply exemplified in the literature and find particular exemplification in Sambrook et al., *Molecular Cloning: A Laboratory Manual,* Cold Spring Harbor Laboratory, Cold Spring Harbor, N.Y., (1982).

Once the vector is completed, the vector may be introduced into plant cells. Techniques for transforming plant cells include microinjection, particle bombardment, direct DNA update, such as using polyethylene glycol, electropotation, viral infection, and transformation with Agrobacterium. For representative techniques, see, D'Halluin et al., *The Plant Cell,* Vol. 4, p. 1495 (1992); Tomes et al., *Plant Mol. Biol.,* Vol. 14, p. 261 (1990); and Zhu et al., *Plant Cell, Tissue and Organ Culture,* Vol. 22, p. 145 (1991).

The nucleotide sequence encoding a given enzyme can be functionally inserted into plants or transiently expressed by virus-based gene delivery systems. Such a system is described in European Patent Application Nos. 67,553, 194,809 and 406,267, PCT WO 93/20217 and U.S. Pat. Nos. 5,304,731 and 5,316,931; which are incorporated herein by reference. Such a system involves delivery of a selected nucleotide sequence as part of, or in conjunction with, a self-replicating DNA or RNA molecule (e.g., a virus), such that the exogenous gene is replicated and expressed during the course of replication and expression of viral or virus-based nucleic acids and proteins. Such gene delivery systems, in addition to enhancing gene "copy number" through the replicative potential of the given virus or virus-based nucleic acids, facilitate the timed delivery of such exogenous genes at the desired state of host development.

An exemplary virus-based gene delivery system employs tobacco mosaic virus. A DNA copy of the virus has a DNA sequence of the present invention inserted therein using conventional techniques of molecular cloning. The cloned DNA copy of the resulting viral vector then is transcribed to produce an RNA. The resulting RNA transcript vector then can be used to inoculate a grown *Nicotiana benthamiana* or *Nicotiana tobacum* plant by applying that RNA transcript onto a carborundum-dusted leaf in the direction of the leaf tip with a gloved finger. The plant so inoculated and infected with the virus vector is allowed to continue growing for about 3 weeks and then is harvested. The harvested plant can be extracted immediately or frozen for storage purposes. This infected plant material, or the vector virions isolated from it, can then be used for the inoculation of a multiplicity of plants for purposes of significantly amplifying the delivered gene or gene product. In order to accomplish this, the leaf tissue so collected is mixed with a 10 mM phosphate buffer (pH 7.5) at a ratio of about 1:10 (w/v). The mixture is macerated using a high speed blender, and centrifuged so as to obtain a liquid inoculum. The inoculum then can be applied to a growing plant, such as a tobacco plant, by applying the inoculum to injured (e.g., lacerated) regions of that plant. For example, the upper most leaves of the growing plant can be cut using an inoculum-wetted cutting blade (e.g., by spray nozzles located in the cutting blade); or the inoculum can be sprayed onto a specific region of one leaf of the plant as a high pressure spray. The plant is allowed to continue growing in order that the viral vector can systemically infect the plant. At a desired stage of infection, the plant is harvested.

The following examples are provided in order to further illustrate the invention but should not be construed as limiting the scope thereof. Unless otherwise noted, all parts and percentages are by weight.

EXAMPLE 1

Isolation of a gene encoding squalene synthetase was carried out as follows:

A. Isolation of RNA from *Nicotiana benthamiana*:

About 100 mg of plant leaf tissue was harvested, transferred to a 1.5 ml microfuge tube, frozen with liquid nitrogen, and homogenized in one ml of AGRIsol (Biogenrex, Houston, Tex.) using a TEFLON® pestle connected to a Moto Tool™ (Dremel Corp., Racine, Wis.). Immediately following homogenization, 100 µl of chloroform was introduced into the tube. The mixture was shaken by hand for 20 sec. Then, the mixture was incubated for 5 min. on ice, and centrifuged for 10 min. at 10,000 ×g at 4° C. The aqueous phase of the centrifuged mixture was transferred to a separate tube, and the RNA was precipitated from that phase by addition of one volume of isopropanol. After incubation on ice for 5 min. that sample was centrifuged for 10 min. at 10,000 ×g at 4° C. The resulting pellet was collected and washed twice with ethanol (75% in water). The pellet was air-dried for about 15 min. The pellet was resuspended in 20 µl RNase-free dH$_2$O. The RNA concentration was calculated by determining the OD$_{260}$ nm(1 OD$_{260}$ nm=40 µg/ml).

B. Isolation of an internal cDNA fragment of squalene synthetase.

The literature was examined for nucleotide or amino acid sequences from human and yeast encoding the gene for squalene synthetase. Regions of conserved amino acid sequence were used to design suitable degenerate oligonucleotide primers. See Robinson et al., *Molecular and Cellular Biology*, Vol. 13, p. 2706 (May 1993). Primers were synthesized from these sequences on an Applied Biosystems Model 391 PCR Mate, or were obtained from commercial sources.

Approximately 150 ng of total RNA was mixed with 10 pg of primer SSP-1, (5'-GGC TCG AGA TIG CCA TIA CYT GNG GNA TNG CXC AXA A-3', where X is G or A, Y is C or T, N is G, A, C, or T, and I is inosine) and dried in a lyophilizer. Five microliters of a 2.5 mM dNTP mix (dATP, dCTP, dGTP, and dTTP) was added to the dried RNA-primer pellet, heated 5 min at 70° C., and cooled to 37° C. The reaction mixture was made up to 10 µl with final concentrations of 50 mM Tris-HCl, pH 8.3, 50 mM KCl, 5 mM MgCl$_2$, 0.5 mM spermidine, and 10 mM DTT. Five units of arian myeloblastosis virus (AMV) reverse transcriptase (Promega, Madison, Wis.) were added and the reaction was incubated for 2 hr at 37° C.

Following first strand cDNA synthesis, 10 pg of primer SSP-2, (5'GGC TCG AGT AYT GYC AYT AYG TIG CNG GIC TNG TNG G-3'), where X is G or A, Y is C or T, N is G, A, C, or T, and I is inosine), was added along with 5 µl of GeneAmp® 10X PCR buffer (500 mM KCl, 100 mM Tris, pH 8.3, 15 mM MgCl$_2$, and 0.01% (w/v) gelatin) (Perkin-Elmer Cetus, Norwalk, Conn.), 30 µl distilled, deionized water, and 5 units AmpliTaq® DNA polymerase (Perkin-Elmer Cetus). PCR amplification was performed using a DNA Thermal Cycler (Perkin-Elmer Cetus) with 1 cycle at 95° C. for 5 min, 35 cycles of 50° C. for 2 min, 72° C. for 2 min, and 95° C. for 2 min, and 1 cycle of 72° C. for 9 min. The amplified products were re-amplified in a 50µl reaction volume with final concentrations of 50 mM KCl, 20 mM Tris-HCl, pH 8.3, 1.5 mM MgCl$_2$, 0.01% (w/v) gelatin, 0.5 mM each of dATP, dGTP, dCTP, dTTP, and 5 units AmpliTaq® DNA polymerase. The re-amplified products were analyzed by separation on a 1% SeaKem® agarose (FMC BioProducts, Rockland, Me.) gel in TAE (1× TAE Buffer is 40 mM Tris-Acetate, 2 mM EDTA) by gel electrophoresis, and a band corresponding to the predicted size of 400 bp was excised and the DNA purified from the gel fragment using Geneclean™ (Bio 101, LaJolla, Calif.).

The isolated 400 bp PCR fragment was cloned into plasmid pCRII (Invitrogen Corporation, San Diego, Calif.). Clones containing the 400 bp insert were subjected to DNA sequence analysis using the Sequenase® Version 2.0 DNA Sequencing Kit (United States Biochemical Corporation, Cleveland, Ohio). A representative clone, designated pSS400, was used for subsequent analysis and manipulation.

DNA sequence was determined by separation of the fragments on a polyacrylamide/urea gel (BioRad, Richmond, Calif.), drying the gel on a sheet of Whatman 3MM paper (Whatman International Ltd., Maidstone England) using a BioRad Model 583 gel dryer. The dried gel was exposed to X-ray film, and the DNA sequence was read. The sequence was examined for homology with the published squalene synthetase sequences. The deduced amino acid sequence encoded by the *Nicotiana benthamiana* squalene synthetase cDNA fragment was found to be 92% homologous to the conserved regions of amino acid sequence reported. See Robinson et al., *Molecular and Cellular Biology*, Vol. 13, p. 2706 (May 1993). All non-identical amino acids in these regions were conserved substitutions.

C. 3' RACE amplification of squalene synthetase.

Sequence data generated from the 400 bp internal squalene synthetase cDNA fragment were used to design additional primers to facilitate the isolation of the complete cDNA. These were synthesized on an Applied Biosystems Model 391 PCR Mate, or were obtained from commercial sources.

Approximately 150 ng of total RNA was heated with 10 pg of Adapter Primer (Gibco BRL, 5'-GGC CAC GCG TCG ACT ACT AC(T)$_{17}$-3') for 10 min. at 65° C. and then chilled 2 min on ice. The reaction mixture was made up to 20 µl total volume with final concentrations of 20 mM Tris-HCl (pH 8.4), 50 mM KCl, 2.5 mM MgCl$_2$, 100 µg/ml BSA, 10 mM DTT, 500 nM Adapter Primer and 0.5 mM each dATP, dCTP, dGTP and dTTP. The mixture was equilibrated 2 min at 42° C. 200 units of SuperScript™ reverse transcriptase were added and the mixture incubated 30 min. at 42° C. Two units of *E. coli* RNase H was added and the mixture incubated 10 min at 42°C. to yield the first strand cDNA.

The first strand cDNA was directly amplified by the PCR method. A 50 µl reaction was assembled with a final composition of 20 mM Tris-HCl (pH 8.4), 50 mM KCl, 2.5 mM, 100 µg/ml BSA, 200 nM primer SSP-3 (5'- TCC ATG GGT TTA TTT CTT GAG -3') 200 nM Universal Amplification Primer (Gibco BRL, 5'-CUA CUA CUA CUA GGC CAC GCG TCG ACT ACT AC -3'), 0.2 mM each dATP, dCTP, dGTP and dTTP, and 5 units AmpliTaq® DNA Polymerase (Perkin-Elmer Cetus). Amplification was in a DNA Thermal Cycler with 1 cycle of 5 min. at 94 °C., 35 cycles of 2 min at 94° C., 2 min at 55° C., 2 min at 72° C., and 1 cycle of 5 min. at 72° C. An aliquot of the amplified PCR products was used directly in a nested amplification performed in a 50 ul reaction with a final composition of 10 mM Tris-HCl (pH 8.3), 50 mM KCl, 1.5 mM, 0.001% (w/v) gelatin, 0.2 mM each dATP, dCTP, dGTP and dTTP, 200 nM Universal Amplification Primer, 200 nM primer SSP-4 (5'-CAA TGT CTA AAT GAG ATG GTC ACT AAT GC- 3'), 1 μl PCR products, and 2.5 units AmpliTaq® DNA Polymerase. Amplification was performed in a DNA Thermal Cycler with 1 cycle of 5 min. at 94° C., 35 cycles of 2 min at 94° C., 2 min at 55° C., 2 min at 72° C., and 1 cycle of 5 min. at 72° C.

D. Southern Analysis of PCR Products:

Nested PCR 3'RACE products were analyzed by separation on a 1% SeaKem® agarose (FMC BioProducts, Rockland, Me.) gel in TAE buffer. The PCR products in the gel were denatured by treatment for 20 min. in 1.5M NaCl, 0.5N NaOH and neutralized by soaking in several volumes of 1.5M NaCl, 1M Tris-HCl (pH 8.0). The PCR products were transferred to a Flash® nylon membrane (Stratagene Cloning Systems, La Jolla, Calif.) using a PosiBlot® pressure blotter (Stratagene) and were UV-crosslinked to the membrane using a Stratalinker® 2400.

Hybridization and detection of squalene synthetase homologous sequences were performed using the chemiluminescent Genius® system (Boehringer Mannheim Biochemicals, Indianapolis, Ind.). The membrane was prehybridized for 1 hr. at 60° C. in 10 ml hybridization solution (5× SSC., 1× Blocking solution, 0.1% N-laurylsarcosinate, 0.02% sodium dodecylsulfate (SDS); 10× Blocking solution is 10%(w/v) Blocking Reagent (Boehringer Mannheim Biochemicals, Indianapolis, Ind.) in 100 mM maleic acid at pH 7.5, 150 mM NaCl). Incubations were in a Model 1040-01-0 rotating bottle hybridization incubator (Robbins Scientific, Sunnyvale, Calif.). Heat-denatured (5 min. at 100° C.) probe was added to the prehybridization mixture at a final concentration of 1.25 ng/ml, and incubation of the resulting mixture was continued 4–16 hr. at 60° C. The membrane was washed twice for 5 min. in 2× SSC., 0.1% SDS at room temperature, and twice for 15 min. in 0.1× SSC., 0.1% SDS at 60° C. For chemiluminescent detection, the membrane was rinsed in 100 mM maleic acid, 150 mM NaCl, and incubated for 30 min. at room temperature in 1× Blocking solution. Alkaline phosphatase-conjugated anti-digoxigenin Fab fragments were added (1:10,000 dilution), and incubation was continued for 30 min. at room temperature. The membrane was washed twice for 15 min. in 100 mM maleic acid, 150 mM NaCl, at room temperature. The membrane was equilibrated for 2 min. in 100 mM Tris-HCl (pH 9.5), 100 mM NaCl, 50 mM MgCl$_2$. The membrane was placed on a sheet of clear acetate film and Lumi-Phos® 530 (Boehringer Mannheim Biochemicals, Indianapolis, Ind.) was added on the DNA side of the membrane. Another sheet of acetate film was used to cover the membrane, and the membrane was exposed to X-ray film. Positive signals on the X-ray film indicated the presence of PCR products containing squalene synthetase homologous sequence.

Chemiluminescent probe for the hybridization procedure was generated by labeling the 400 bp insert sequences of plasmid pSS400. One μg of plasmid pSS400 was digested with EcoRI to excise the insert. The squalene synthetase cDNA fragment was separated on an agarose gel and excised after visualization by ethidium bromide staining. The DNA was purified from the gel fragment using GeneClean and resuspended in 14 μl dH$_2$O. The DNA was heat-denatured 10 min at 100° C. and chilled on ice. The Genius® Kit 2 (Boehringer Mannheim Biochemicals) was used to label the fragment with digoxigenin-dUTP according to the manufacturer's protocols. The probe concentration was determined by comparison with a dilution series of a known standard on a Flash® membrane, detected by chemiluminescence as above.

E. Cloning of the 3' RACE products.

The nested PCR 3' RACE products of squalene synthetase were cloned using the pCRII vector. Clones were screened by digestion with EcoRI to liberate the insert, separation on an agarose gel, transfer to a nylon membrane, and hybridization and detection as described above. Clones exhibiting a positive hybridization signal were subjected to DNA sequence analysis as described above. The sequence was examined for homology with the published squalene synthetase sequences. Clones were identified that exhibited at least 90% homology to the conserved regions in other squalene synthetase genes.

F. 5' RACE amplification and cloning of squalene synthetase.

The 5' RACE procedure (Frohman et al., *Proc. Nat. Acad. Sci. USA*, Vol. 85, pp. 8998 –9002 (1988)) was used to amplify the 5' terminus of squalene synthetase mRNA.

Four to six μg total *Nicotiana benthamiana* RNA was combined with 10 pmole of primer SSP-5 (5 '- GTA AGT CAA ACA ATC TTC TAC ATG TGA-3') and the mix was heated for 10 min at 70° C. and chilled on ice. The reaction was brought to a volume of 20 μl in 20 mM Tris-HCl (pH 8.4, 50 mM KCl, 2.5 mM MgCl$_2$, 0.1 mg/ml BSA, 10 mM DTT, 0.2 mM each dATP, dCTP, dGTP and dTTP, and 200 units reverse transcriptase. The mixture was incubated for 10 min at room temperature and 50 min at 42° C. The reaction was stopped by heating for 5 min at 90° C. and chilled on ice. Two units *E. coli* RNAse H were added and the reaction incubated 20 min at 37° C. The single-stranded cDNA was purified from the previous reaction using Geneclean™, resuspended in 16 μl dH$_2$O, heated 10 min at 70° C. and chilled on ice. The tailing reaction was initiated by adding 1 μl of 10× reaction buffer (200 mM Tris-HCl, (pH 8.4), 500 mM KCl, 25 mM MgCl$_2$, 1 mg/ml BSA), 2 μl 2 mM CTP, and 15 units of terminal transferase (TdT) to the single-stranded cDNA. After 10 min at 37° C., the TdT was inactivated for 10 min at 70° C. and the reaction chilled on ice.

Ten μl of the dC-tailed cDNA was used in the amplification step. The volume of the reaction was brought to 100 μl by the addition of 76.5 μl dH$_2$O, 9.5 μl 10× reaction buffer, 0.2 mM each dATP, dCTP, dGTP and dTTP, 10 pmole primer SSP-6 (5'- CTG AAG AAA TAA ACC CAT GGA -3'), 10 pmole Anchor primer (Gibco BRL, 5'-CUA CUA CUA CUA GGC CAC GCG TCG ACT AGT ACG GGI IGG GII GGG IIG- 3') and 5 units Taq DNA polymerase (Gibco BRL). The amplification was performed with one cycle of 2 min at 94° C., 37 cycles of 30 sec at 94° C., 15 sec at 55° C., 40 sec at 72° C., and one cycle at 72° C. for 5 min. The amplification products were analyzed by agarose gel electrophoresis and a DNA fragment of approximately 800 bp was visualized after ethidium bromide staining.

One microliter of the first reaction was amplified by PCR using the Universal Amplification Primer (UAP) (Gibco BRL, 5'- CUA CUA CUA CUA GGC CAC GCG TCG ACT ACT AC -3'). The reaction was composed of 80.5 μl dH$_2$O, 10 μl 10× Taq polymerase buffer (Gibco BRL), 5 μl 50 mM MgCl$_2$, μl of the DNA Polymerization Mix (Pharmacia LKB Biotechnology, Piscataway, N.J.), 1 μl of the first amplification reaction, and 2.5 units Taq polymerase. The amplification was performed with one cycle of 2 min at 94 C., 30 cycles of 40 sec at 94 C., 30 sec at 55° C., 1 min at 72° C., and one cycle at 72° C. for 5 min. The amplified products were purified using a Magic PCR Prep® column (Promega, Madison, Wis.) as recommended by the manufacturer followed by agarose gel electrophoresis. The resulting 800 bpDNA fragment was excised from the agarose and purified using GeneClean. The fragment was cloned into a pCRII vector using standard cloning techniques. The clones were subjected to DNA sequence analysis using the Sequenase Version 2.0 DNA Sequencing Kit (United States Biochemical Corporation, Cleveland, Ohio). The sequence was examined for homology with the published squalene synthetase sequences. Clones were detected that exhibited at least 90% homology to the conserved regions in other squalene synthetase genes.

G. Cloning of Squalene Synthetase.

A region of the squalene synthetase encompassing the start codon and the stop codon was amplified using the PCR as follows: Total RNA from 500 mg of fresh leaves of *Nicotiana benthamiana* was extracted with Trizol™ RNA extraction kit (Gibco BRL). The first DNA strand was synthesized by a reverse transcription reaction using 6 µg of total RNA as a template, oligo(dT)$_{12-18}$ as primer (0.5 µg), and the SuperScript™ preamplification kit (Gibco BRL). The RNA-primer mix was brought to a total volume of 14 µl, heated for 10 min at 70° C, then chilled on ice. The reaction volume was adjusted to 20 µl by adding 2µl of 10× synthesis buffer (200 mM Tris-HCl (pH 8.4), 500 mM KCl, 25 mM MgCl$_2$, 1 mg/ml BSA), 21µl of 0.1 M DTT, 1 µl of 10 mM dNTP mix and 1 µl (200 units) of reverse transcriptase. The mixture was incubated for 10 min at room temperature and 50 min at 42° C. The reaction was stopped by heating 5 min at 90° C. and chilled on ice. Then, 1 µl of *E. coli* RNAse H (two units) was added and the mixture incubated 20 min at 37° C.

For the polymerase chain reaction (PCR) step, two primers (10 pmole of each) were added (SSP-7 (5' - CAA CGC TTT CTC CTC TTA CCA -3') and SSP-8 (5' - CGT CTA AGA TCG GTT TCC GGA -3')) and the reaction mix volume increased to 100 µl with 8 µl of 10 × synthesis buffer, 0.5 µl of Taq DNA polymerase and water. PCR was performed using 94° C. for 40 sec, 55° C. for 20 sec and 72° C. for 1 min for 35 cycles, and 94° C. for 40 sec, 55° C. for 20 sec and 72° C. for 6 min for one cycle.

Figure 1:
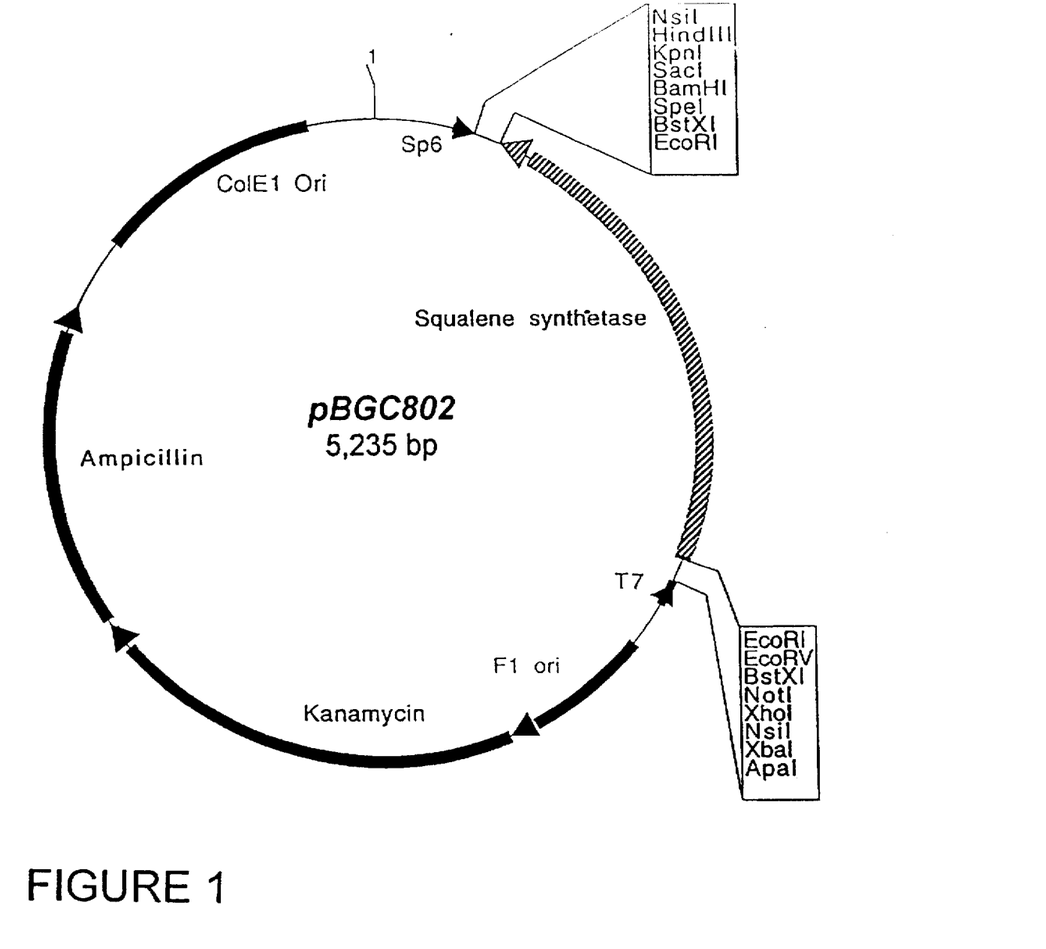
FIGS. 1 and 2 illustrate maps of plasmids pBGC802 and pBGC803, respectively, which each contain the *Nicotiana benthamiana* squalene synthetase gene cloned in as a PCR fragment into plasmid pCRII (Invitrogen, San Diego, Calif.).

The PCR products were analyzed by agarose gel electrophoresis. A DNA fragment of the expected size of 1275 bp was excised from the agarose gel, and purified using GeneClean. The PCR product was then ligated to the pCR II using the manufacturer's recommendations. Following transformation, fourteen colonies were analyzed by plasmid DNA isolation and digestion with Eco RI. Plasmid DNA from three independant clones containing the expected 1275 bp insert were purified using the Wizard midiprep purification kit (Promega Corp.) and the sequences determined. A single example (designated pBGC802, FIG. 1) was chosen and used as a template for specific amplification of the coding region.

Amplification of the squalene synthetase coding region was carried out as follows: Plasmid pBGC802 (10 ng) was used as a template in amplification by PCR using primers SSP-9 (5' - GCG CAT ATG GGG ACT TTG AGG GCT ATT CT-3') and SSP-10 (5' - CGA GTC GAC TAA GAT CGG TTT CCG GAT AG -3'). Primer SSP-9 was homologous to squalene synthetase gene sequences containing the translational initiation codon. Additionally, several nucleotides were changed to introduce an Nde I restriction site in the primer. Primer SSP-10 was complementary to squalene synthetase gene sequences containing the translational termination codon with several nucleotides changed to create a Sal I restriction site downstream from the stop codon.

The amplification reactions consisted of 80.5 µl of water, 10 µl of 10× Taq DNA polymerase buffer (Gibco BRL), 5 µl of MgCl$_2$ 50 mM, 1µl (10 pmole) of each primer SSP-9 and SSP-10, 1 µl of the DNA Polymerization Mix, 1 µl of the uncut plasmid DNA (pBSG802 at 10 ng/µl) and 0.5 µl (2.5 units) of Taq DNA Polymerase (Gibco BRL). The amplifications were performed with 4 min incubation at at 94° C.; 2 cycles of 40 sec at 94° C., 20 sec at 45° C., 1 min at 72° C.; 20 cycles of 40 sec at 94° C., 20 sec at 55° C., 1 min at 72° C.; and 5 min incubation at 72° C.

Figure 2:
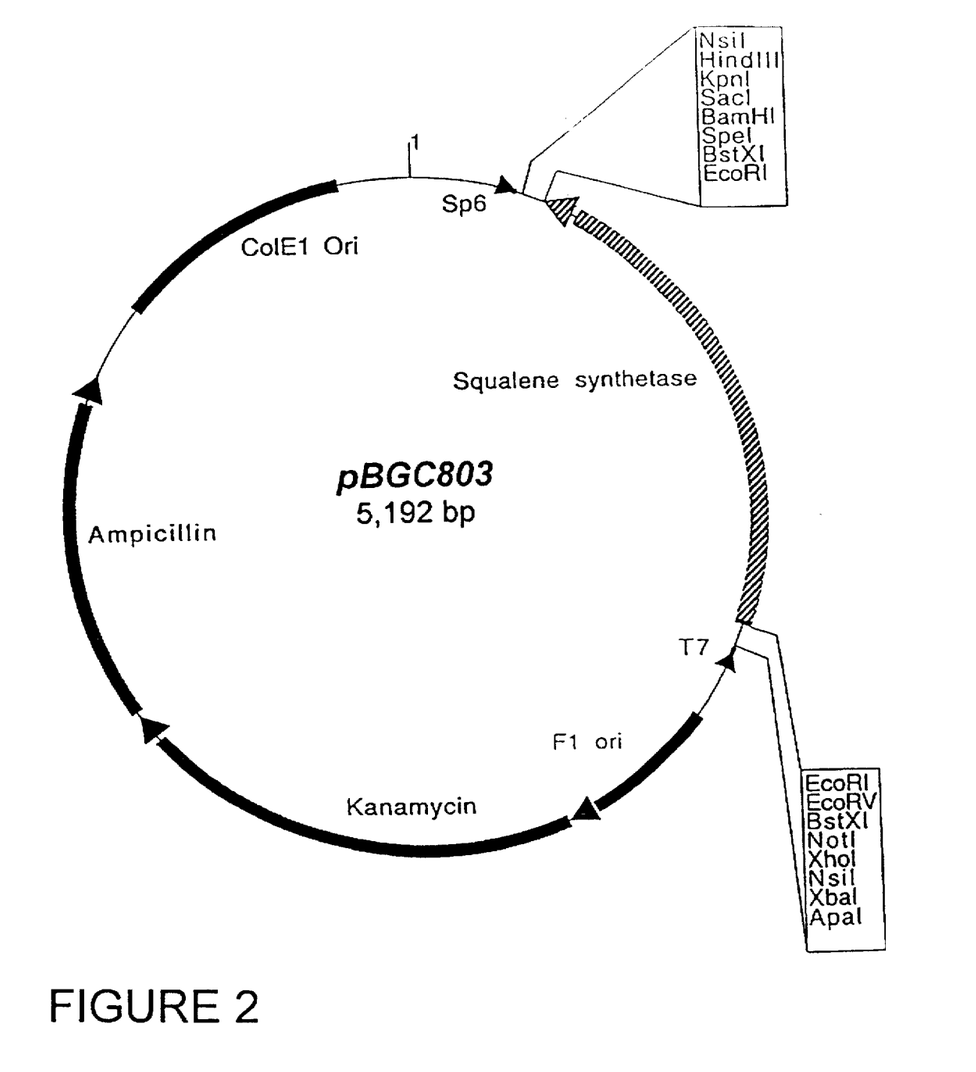

The amplified products were analyzed by agarose gel electrophoresis and the single DNA fragment of 1240 bp was purified using GeneClean®. The PCR products were ligated to the pCR II vector using the directions of the manufacturer. The ligation products were used to transform *E. coli* competent cells (OneShot™ INVαF'competent cells, Invitrogn Corp. Analysis of plasmid DNA from the resulting bacterial colonies revealed an insert of approximately 1245 bp. Plasmid DNA was purified using the Wizard midiprep purification kit and the DNA sequence determined. The resulting clone, designated pBGC803 (FIG. 2), thus consisted primarily of the *Nicotiana benthamiana* squalene synthetase coding region.

Figure 3:
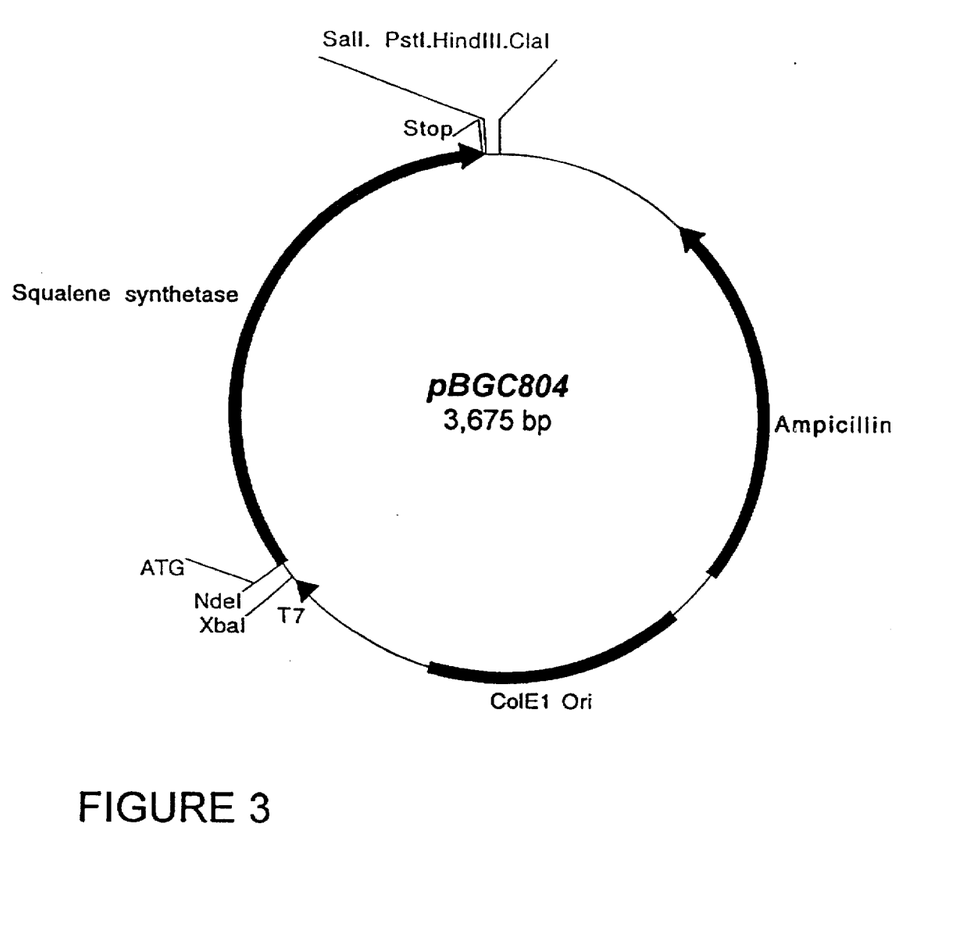
FIG. 3 illustrates a map of the plasmid pBGC804 containing the *Nicotiana benthamiana* squalene synthetase gene cloned as an NdeI/SalI fragment into the expression vector pT7-7.
Figure 4:
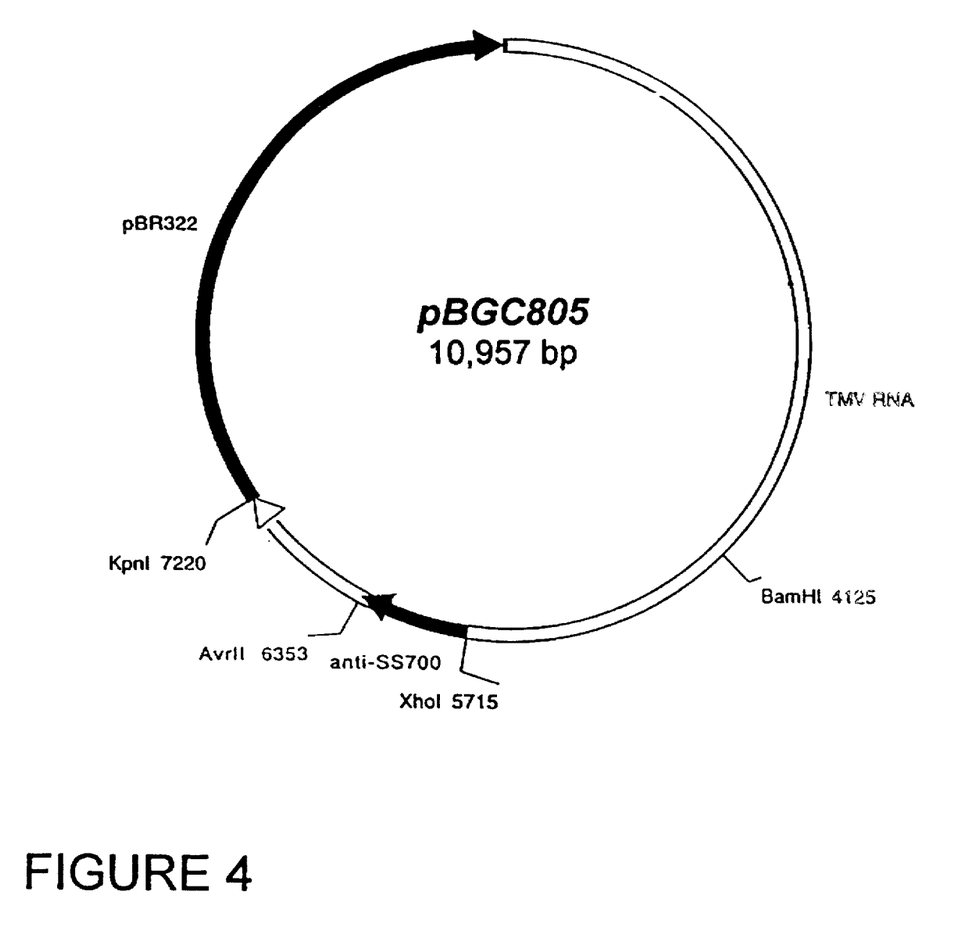
FIG. 4 illustrates a map of the transcription plasmid pBGC805 containing a 638 bp antisense fragment of *Nicotiana benthamiana* squalene synthetase cloned into the XhoI and AvrII sites of the RNA viral vector TTO 1A.

Cloning of the squalene synthetase gene in a bacterial expression vector was carried out as follows:

Plasmid pBGC803 was cut with Sal I and with Nde I in order to excise the squalene synthetase coding region. The digestion products were analyzed by agarose gel electrophoresis and the 1240 bp DNA fragment purified using GeneClear®. Plasmid p77-7 (Tabor et al., *Proc. Nat. Acad. Sci. USA*, Vol. 82, p. 1074 (1985)) was cut with Nde I and Sal I and the squalene synthetase coding region was inserted followed by transformation of DH 10B competent cells (Gibco BRL). One of the resulting clones, designated pBGC804 (FIG. 3), contains the Nde I/Sal I DNA fragment of clone pBGC803.

Competent cells of bacterial strain BL21 (DE3) ( Novagen, Inc., Madison, Wis.) were transformed with plasmid pBGC804. A culture was started from a well isolated colony in media containing 50 µg/ mL of ampicillin. When the OD$_{600}$was approximately equal to 0.4, IPTG was added to a final concentration of 0.4 mM. The culture was maintained at 37° C. with agitation. At 0, 10 min, 30 min, 60 min, 90 min, 120 min and 240 min post-induction with IPTG, aliquots of 1.5 mL were taken and the cells pelleted at 14, 000 rpm for 3 min. The cell pellet was then resuspended with 100 µl of 1× loading buffer and 10 µl of each aliquot was analyzed for total protein content using a 12% % SDS-polyacrylarnide precast gel (Novex, San Diego, Calif.). A protein of approximately 45 kDa increased in intensity from time 0 to time 240 min post-induction with IPTG. The calculated molecular weight for the squalene synthetase protein is 47.073.

EXAMPLE 2

Insertion of a 700 bp antisense *Nicotiana benthamiana* squalene synthetase sequence into a virus-based gene expression system and expression in transfected plants was accomplished as follows:

A. Insertion of the squalene synthetase gene into an RNA viral vector: RNA viral vector TTOIA was constructed as follows:

An 861 bp fragment from tomato mosaic virus virion RNA (fruit necrotic strain F; ToMV-F) was isolated by RT-PCR using ToMV primers 5'- CTC GCA AAG TTT GGA ACC AAA TCC TC -3' (upstream) and 5'-CGG GGT ACC TGG GCC CCA ACC GGG GGT TCC GGG GG- 3'(downstream) and subcloned into the HincII site of pBluescript KS- (Stratagene. LaJ

|     |     |     |     |     |     |     |     |     |     |     |     |     |     |     |     |     |
|-----|-----|-----|-----|-----|-----|-----|-----|-----|-----|-----|-----|-----|-----|-----|-----|-----|
| | | 35 | | | | 40 | | | | | 45 | | | | 50 | |
| TTT | GCT | CTC | GTC | ATT | CAA | CAA | CTT | CCA | GTC | GAG | CTT | CGT | GAC | GCC | GTG | 309 |
| Phe | Ala | Leu | Val | Ile | Gln | Gln | Leu | Pro | Val | Glu | Leu | Arg | Asp | Ala | Val | |
| | | | | 55 | | | | | 60 | | | | | 65 | | |
| TGC | ATT | TTC | TAT | TTG | GTT | CTT | CGA | GCA | CTT | GAC | ACT | GTT | GAG | GAT | GAT | 357 |
| Cys | Ile | Phe | Tyr | Leu | Val | Leu | Arg | Ala | Leu | Asp | Thr | Val | Glu | Asp | Asp | |
| | | | 70 | | | | | 75 | | | | | 80 | | | |
| ACC | AGC | ATT | CCC | ACC | GAT | GTT | AAA | GTT | CCT | ATT | CTG | ATC | TCT | TTT | CAT | 405 |
| Thr | Ser | Ile | Pro | Thr | Asp | Val | Lys | Val | Pro | Ile | Leu | Ile | Ser | Phe | His | |
| | | 85 | | | | | 90 | | | | | 95 | | | | |
| CAG | CAT | GTT | TAT | GAT | CGC | GAA | TGG | CAT | TTT | TCA | TGT | GGT | ACA | AAG | GAG | 453 |
| Gln | His | Val | Tyr | Asp | Arg | Glu | Trp | His | Phe | Ser | Cys | Gly | Thr | Lys | Glu | |
| | | 100 | | | | 105 | | | | | 110 | | | | | |
| TAC | AAG | GTT | CTC | ATG | GAC | CAG | TTC | CAT | CAT | GTA | TCA | ACT | GCT | TTT | CTG | 501 |
| Tyr | Lys | Val | Leu | Met | Asp | Gln | Phe | His | His | Val | Ser | Thr | Ala | Phe | Leu | |
| 115 | | | | 120 | | | | | 125 | | | | | | 130 | |
| GAG | CTT | AGG | AAA | CAT | TAT | CAG | CAG | GCA | ATT | GAG | GAT | ATT | ACC | ATG | AGG | 549 |
| Glu | Leu | Arg | Lys | His | Tyr | Gln | Gln | Ala | Ile | Glu | Asp | Ile | Thr | Met | Arg | |
| | | | | 135 | | | | | 140 | | | | | 145 | | |
| ATG | GGT | GCA | GGA | ATG | GCA | AAA | TTC | ATA | TGC | AAG | GAG | GTG | GAA | ACA | ACC | 597 |
| Met | Gly | Ala | Gly | Met | Ala | Lys | Phe | Ile | Cys | Lys | Glu | Val | Glu | Thr | Thr | |
| | | | 150 | | | | | 155 | | | | | 160 | | | |
| GAT | GAT | TAT | GAC | GAA | TAT | TGT | CAC | TAT | GTA | GCT | GGG | CTT | GTT | GGG | CTA | 645 |
| Asp | Asp | Tyr | Asp | Glu | Tyr | Cys | His | Tyr | Val | Ala | Gly | Leu | Val | Gly | Leu | |
| | | | 165 | | | | | 170 | | | | | 175 | | | |
| GGA | TTG | TCA | AAA | CTG | TTC | CAT | GCC | TCT | GAG | AAA | GAA | GAT | CTG | GCT | TCA | 693 |
| Gly | Leu | Ser | Lys | Leu | Phe | His | Ala | Ser | Glu | Lys | Glu | Asp | Leu | Ala | Ser | |
| | 180 | | | | | 185 | | | | | 190 | | | | | |
| GAT | TCT | CTC | TCC | AAC | TCC | ATG | GGT | TTA | TTT | CTT | CAG | AAA | ACA | AAC | ATC | 741 |
| Asp | Ser | Leu | Ser | Asn | Ser | Met | Gly | Leu | Phe | Leu | Gln | Lys | Thr | Asn | Ile | |
| 195 | | | | | 200 | | | | | 205 | | | | | 210 | |
| ATT | AGA | GAT | TAT | TTG | GAA | GAC | ATA | AAT | GAA | GTA | CCC | AAG | TGC | CGT | ATG | 789 |
| Ile | Arg | Asp | Tyr | Leu | Glu | Asp | Ile | Asn | Glu | Val | Pro | Lys | Cys | Arg | Met | |
| | | | | 215 | | | | | 220 | | | | | 225 | | |
| TTC | TGG | CCC | CGT | GAA | ATA | TGG | AGT | AAA | TAT | GTT | AAC | AAG | CTT | GAG | GAA | 837 |
| Phe | Trp | Pro | Arg | Glu | Ile | Trp | Ser | Lys | Tyr | Val | Asn | Lys | Leu | Glu | Glu | |
| | | | 230 | | | | | 235 | | | | | 240 | | | |
| TTA | AAG | TAC | GAG | GAT | AAC | TCG | GCC | AAA | GCA | GTG | CAA | TGT | CTA | AAT | GAC | 885 |
| Leu | Lys | Tyr | Glu | Asp | Asn | Ser | Ala | Lys | Ala | Val | Gln | Cys | Leu | Asn | Asp | |
| | | 245 | | | | | 250 | | | | | 255 | | | | |
| ATG | GTC | ACT | AAT | GCT | TTA | TCA | CAT | GTA | GAA | GAT | TGT | TTG | ACT | TAC | ATG | 933 |
| Met | Val | Thr | Asn | Ala | Leu | Ser | His | Val | Glu | Asp | Cys | Leu | Thr | Tyr | Met | |
| | 260 | | | | | 265 | | | | | 270 | | | | | |
| TCT | GCT | TTG | CGT | GAT | CCT | TCC | ATC | TTT | CGA | TTC | TGT | GCT | ATT | CCA | CAG | 981 |
| Ser | Ala | Leu | Arg | Asp | Pro | Ser | Ile | Phe | Arg | Phe | Cys | Ala | Ile | Pro | Gln | |
| 275 | | | | | 280 | | | | | 285 | | | | | 290 | |
| GTC | ATG | GCA | ATT | GGG | ACA | TTA | GCT | ATG | TGC | TAC | GAC | AAC | ATT | GAA | GTC | 1029 |
| Val | Met | Ala | Ile | Gly | Thr | Leu | Ala | Met | Cys | Tyr | Asp | Asn | Ile | Glu | Val | |
| | | | | 295 | | | | | 300 | | | | | 305 | | |
| TTC | AGA | GGA | GTG | GTA | AAA | ATG | AGA | CGT | GGT | CTG | ACT | GCT | AAG | GTC | ATT | 1077 |
| Phe | Arg | Gly | Val | Val | Lys | Met | Arg | Arg | Gly | Leu | Thr | Ala | Lys | Val | Ile | |
| | | | 310 | | | | | 315 | | | | | 320 | | | |
| GAC | CGG | ACC | AGG | ACT | ATT | GCA | GAT | GTA | TAT | GGT | GCT | TTT | TTT | GAC | TTT | 1125 |
| Asp | Arg | Thr | Arg | Thr | Ile | Ala | Asp | Val | Tyr | Gly | Ala | Phe | Phe | Asp | Phe | |
| | | 325 | | | | | 330 | | | | | 335 | | | | |
| TCT | TGT | ATG | CTG | AAA | TCC | AAG | GTT | AAT | AAT | AAT | GAT | CCA | AAT | GCA | ACA | 1173 |
| Ser | Cys | Met | Leu | Lys | Ser | Lys | Val | Asn | Asn | Asn | Asp | Pro | Asn | Ala | Thr | |
| | | 340 | | | | | 345 | | | | | 350 | | | | |
| AAA | ACT | CTG | AAG | AGG | CTC | GAA | GTG | ATC | CTG | AAA | ACT | TGC | AGA | GAT | TCG | 1221 |
| Lys | Thr | Leu | Lys | Arg | Leu | Glu | Val | Ile | Leu | Lys | Thr | Cys | Arg | Asp | Ser | |

| | | | | | | | | | | | | | | | | |
|---|---|---|---|---|---|---|---|---|---|---|---|---|---|---|---|---|
|355| | | | | |360| | | | |365| | | |370| |
|GGA|ACC|TTG|AAC|AAA|AGG|AAA|TCC|TAC|ATA|ATC|AGG|AGC|GAG|CCT|AAT|1269|
|Gly|Thr|Leu|Asn|Lys|Arg|Lys|Ser|Tyr|Ile|Ile|Arg|Ser|Glu|Pro|Asn| |
| | | | |375| | | |380| | | |385| | | | |
|TAC|AGT|CCA|GTT|CTG|ATT|GTT|GTC|ATT|TTC|ATC|ATA|CTG|GCT|ATT|ATT|1317|
|Tyr|Ser|Pro|Val|Leu|Ile|Val|Val|Ile|Phe|Ile|Ile|Leu|Ala|Ile|Ile| |
| | | |390| | | |395| | | |400| | | | | |
|CTC|GCA|CAG|CTA|TCC|GGA|AAC|CGA|TCT|TAGACGATAT|TTTGGGTTAC| | | | | |1364|
|Leu|Ala|Gln|Leu|Ser|Gly|Asn|Arg|Ser| | | | | | | | |
| | | |405| | | |410| | | | | | | | | |

```
AAAAAGAAG  TCTGGTCAAG  GAAGACAGCA  GAAGCTCTTG  GCCAATTGTG  TGATTAGTGC   1424
AGATTTTGAT  GTTTGTAATT  CTATCGTCCA  TTAAGTGATA  GTTGCACCTT  TTAACCTGAC   1484
AAGATAATTA  CGAAGACCTA  TTTTGGTGG   TTTGTTGGGT  ATGTACTTGT  TTGCAAGGCT   1544
ACGTAAGCAA  ATTCCAAGTG  TTGTAGAGTC  ACCGTGATGT  AATAAACATG  TCTTTTATTA   1604
TAGTTTGTTC  ATTTTGTGG   TAAAAAAAAA  AAAAAAA                              1642
```

( 2 ) INFORMATION FOR SEQ ID NO:2:

( i ) SEQUENCE CHARACTERISTICS:
        ( A ) LENGTH: 411 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:2:

```
Met  Gly  Ser  Leu  Arg  Ala  Ile  Leu  Lys  Asn  Pro  Glu  Asp  Leu  Tyr  Pro
 1              5                        10                       15

Leu  Val  Lys  Leu  Lys  Leu  Ala  Ala  Arg  His  Ala  Glu  Lys  Gln  Ile  Pro
          20                       25                       30

Pro  Ser  Pro  Asn  Trp  Gly  Phe  Cys  Tyr  Ser  Met  Leu  His  Lys  Val  Ser
     35                       40                       45

Arg  Ser  Phe  Ala  Leu  Val  Ile  Gln  Gln  Leu  Pro  Val  Glu  Leu  Arg  Asp
50                       55                       60

Ala  Val  Cys  Ile  Phe  Tyr  Leu  Val  Leu  Arg  Ala  Leu  Asp  Thr  Val  Glu
65                       70                       75                       80

Asp  Asp  Thr  Ser  Ile  Pro  Thr  Asp  Val  Lys  Val  Pro  Ile  Leu  Ile  Ser
                    85                       90                       95

Phe  His  Gln  His  Val  Tyr  Asp  Arg  Glu  Trp  His  Phe  Ser  Cys  Gly  Thr
               100                      105                      110

Lys  Glu  Tyr  Lys  Val  Leu  Met  Asp  Gln  Phe  His  His  Val  Ser  Thr  Ala
          115                      120                      125

Phe  Leu  Glu  Leu  Arg  Lys  His  Tyr  Gln  Gln  Ala  Ile  Glu  Asp  Ile  Thr
130                      135                      140

Met  Arg  Met  Gly  Ala  Gly  Met  Ala  Lys  Phe  Ile  Cys  Lys  Glu  Val  Glu
145                      150                      155                      160

Thr  Thr  Asp  Asp  Tyr  Asp  Glu  Tyr  Cys  His  Tyr  Val  Ala  Gly  Leu  Val
               165                      170                      175

Gly  Leu  Gly  Leu  Ser  Lys  Leu  Phe  His  Ala  Ser  Glu  Lys  Glu  Asp  Leu
          180                      185                      190

Ala  Ser  Asp  Ser  Leu  Ser  Asn  Ser  Met  Gly  Leu  Phe  Leu  Gln  Lys  Thr
          195                      200                      205

Asn  Ile  Ile  Arg  Asp  Tyr  Leu  Glu  Asp  Ile  Asn  Glu  Val  Pro  Lys  Cys
     210                      215                      220

Arg  Met  Phe  Trp  Pro  Arg  Glu  Ile  Trp  Ser  Lys  Tyr  Val  Asn  Lys  Leu
225                      230                      235                      240
```

-continued

| Glu | Glu | Leu | Lys | Tyr 245 | Glu | Asp | Asn | Ser | Ala 250 | Lys | Ala | Val | Gln | Cys 255 | Leu |
| --- | --- | --- | --- | --- | --- | --- | --- | --- | --- | --- | --- | --- | --- | --- | --- |
| Asn | Asp | Met | Val 260 | Thr | Asn | Ala | Leu | Ser 265 | His | Val | Glu | Asp | Cys 270 | Leu | Thr |
| Tyr | Met | Ser 275 | Ala | Leu | Arg | Asp | Pro 280 | Ser | Ile | Phe | Arg | Phe 285 | Cys | Ala | Ile |
| Pro | Gln 290 | Val | Met | Ala | Ile | Gly 295 | Thr | Leu | Ala | Met | Cys 300 | Tyr | Asp | Asn | Ile |
| Glu 305 | Val | Phe | Arg | Gly | Val 310 | Val | Lys | Met | Arg | Arg 315 | Gly | Leu | Thr | Ala | Lys 320 |
| Val | Ile | Asp | Arg | Thr 325 | Arg | Thr | Ile | Ala | Asp 330 | Val | Tyr | Gly | Ala | Phe 335 | Phe |
| Asp | Phe | Ser | Cys 340 | Met | Leu | Lys | Ser | Lys 345 | Val | Asn | Asn | Asn | Asp 350 | Pro | Asn |
| Ala | Thr | Lys 355 | Thr | Leu | Lys | Arg | Leu 360 | Glu | Val | Ile | Leu | Lys 365 | Thr | Cys | Arg |
| Asp | Ser 370 | Gly | Thr | Leu | Asn | Lys 375 | Arg | Lys | Ser | Tyr | Ile 380 | Ile | Arg | Ser | Glu |
| Pro 385 | Asn | Tyr | Ser | Pro | Val 390 | Leu | Ile | Val | Val | Ile 395 | Phe | Ile | Ile | Leu | Ala 400 |
| Ile | Ile | Leu | Ala | Gln 405 | Leu | Ser | Gly | Asn | Arg 410 | Ser | | | | | |

What is claimed is:

1. An isolated nucleotide molecule encoding squalene synthetase having an amino acid sequence specified by SEQ ID NO:2, which nucleotide molecule is isolated from a Nicotiana species.

2. The nucleotide molecule of claim 1 in the form of DNA.

3. The nucleotide sequence of claim 2 isolated from Nicotiana benthamiana.

4. An isolated nucleotide molecule encoding squalene synthetase having an amino acid sequence specified by SEQ ID NO:2.

5. The nucleotide molecule of claim 4 in the form of DNA.

6. The nucleotide sequence of claim 5 isolated from a Nicotiana species.

7. The nucleotide sequence of claim 5 isolated from Nicotiana benthamiana.

8. An isolated nucleotide molecule encoding squalene synthetase, which nucleotide molecule is either identical to, complementary to, or a transcribed RNA equivalent of SEQ ID NO:1.

9. The nucleotide molecule of claim 8 in the form of DNA.

10. The nucleotide sequence of claim 9 isolated from a Nicotiana species.

11. The nucleotide sequence of claim 9 isolated from Nicotiana benthamiana.

* * * * *